(12) United States Patent
Sato

(10) Patent No.: US 6,798,863 B2
(45) Date of Patent: Sep. 28, 2004

(54) COMBINED X-RAY ANALYSIS APPARATUS

(75) Inventor: Masao Sato, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 10/147,421

(22) Filed: May 16, 2002

(65) Prior Publication Data

US 2002/0191747 A1 Dec. 19, 2002

(30) Foreign Application Priority Data

May 29, 2001 (JP) ........................................ 2001-160848

(51) Int. Cl.⁷ ..................... G01N 23/20; G01N 23/223; H01J 35/08
(52) U.S. Cl. ............................. 378/46; 378/90; 378/143
(58) Field of Search .................................. 378/143, 124, 378/46, 45, 44, 70, 71, 82, 83, 90

(56) References Cited

U.S. PATENT DOCUMENTS

| | | | | |
|---|---|---|---|---|
| 4,521,905 A | * | 6/1985 | Hosokawa | 378/206 |
| 4,622,688 A | * | 11/1986 | Diemer et al. | 378/143 |
| 4,646,338 A | * | 2/1987 | Skillicorn | 378/110 |
| 5,014,287 A | * | 5/1991 | Thornton et al. | 378/45 |
| 5,166,966 A | * | 11/1992 | Steinmeyer | 378/156 |
| 5,247,562 A | * | 9/1993 | Steinbach | 378/119 |
| 5,406,608 A | * | 4/1995 | Yellepeddi et al. | 378/46 |
| 5,491,738 A | * | 2/1996 | Blake et al. | 378/71 |
| 5,745,543 A | * | 4/1998 | De Bokx et al. | 378/45 |
| 6,477,226 B1 | * | 11/2002 | Lehmann et al. | 378/44 |
| 2002/0097834 A1 | * | 7/2002 | Satoh | 378/46 |

FOREIGN PATENT DOCUMENTS

| | | | | |
|---|---|---|---|---|
| JP | 06-258061 | * | 9/1994 | ........... G01B/15/02 |
| JP | 06258260 A | * | 9/1994 | ......... G01N/23/207 |
| JP | 09072864 A | * | 3/1997 | ......... G01N/23/207 |
| JP | 10048159 A | * | 2/1998 | ......... G01N/23/207 |
| JP | 11006806 A | * | 1/1999 | ......... G01N/23/207 |
| JP | 11-044662 | * | 2/1999 | .......... G01N/23/20 |
| JP | 2001013095 A | * | 1/2001 | ......... G01N/23/207 |

* cited by examiner

Primary Examiner—David V. Bruce
Assistant Examiner—Chih-Cheng Glen Kao
(74) Attorney, Agent, or Firm—Adams & Wilks

(57) ABSTRACT

In order to provide a single, small apparatus capable of elemental and structural analysis of inorganic matter by utilizing X-rays having non-obstructive and non-contact characteristics there is provided a small, energy distribution type X-ray detector for detecting X-ray fluorescence and subjecting the X-ray fluorescence to elemental and quantative analysis, and a CCD line sensor for performing structural analysis. An X-ray tube target structure that is a Cu layer on an Mo layer is adopted. When excitation is performed using a low accelerating voltage, this is made monochromatic by using a Cu filter to filter the Cu—K lines and the continuous X-rays generated, with the radiation quality (Cu—K lines) thus generated then being utilized in X-ray diffraction. When excitation is performed using a high accelerating voltage, Cu—K lines of the Cu—K lines, Mo—K lines and continuous X-rays thus generated are blocked by absorption using an Mo or Zr filter, with the Mo—K lines and continuous X-rays thus obtained being utilized in X-ray fluorescence analysis.

10 Claims, 2 Drawing Sheets

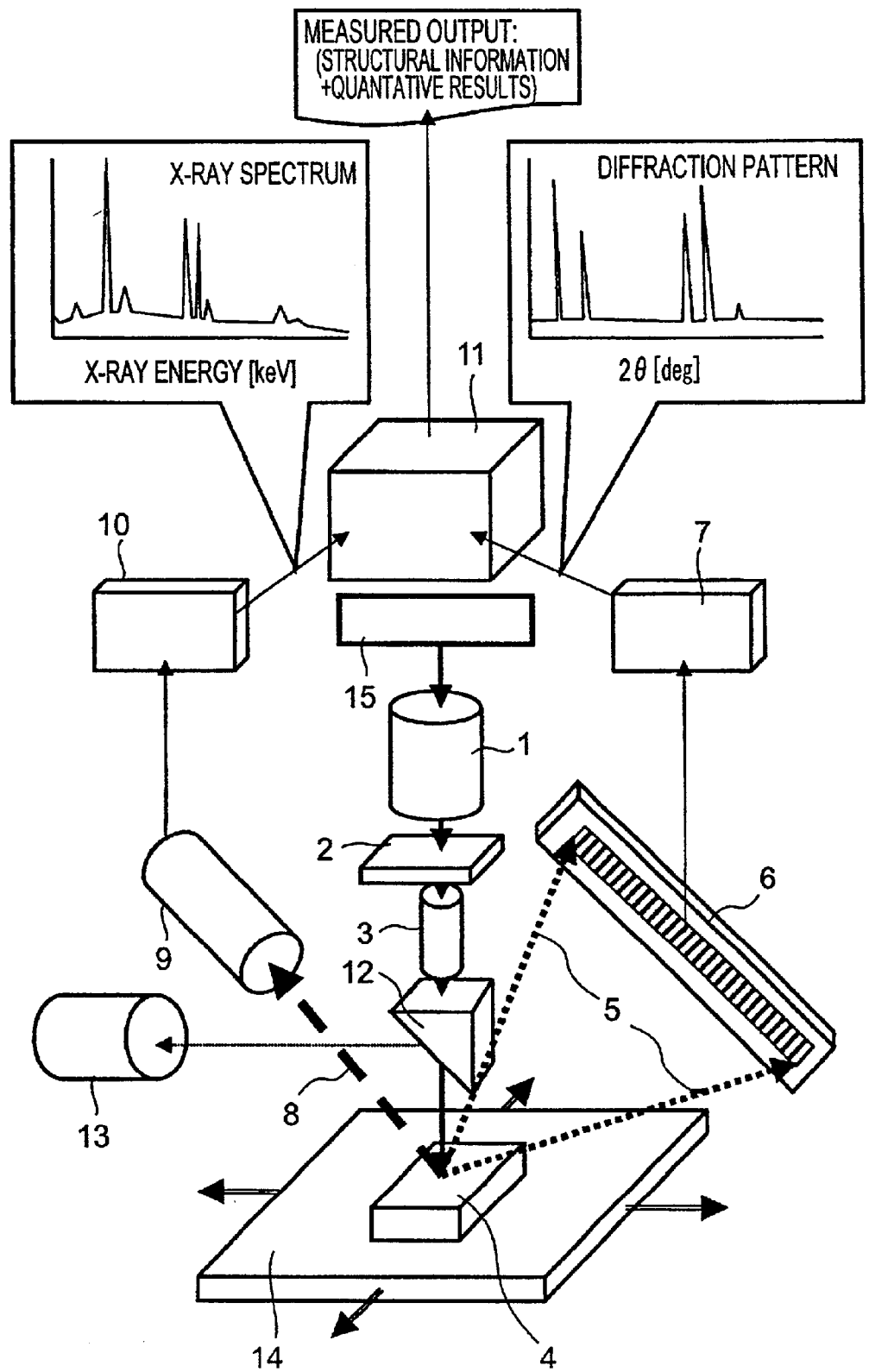

COMBINED X-RAY ANALYSIS APPARATUS

BACKGROUND OF THE INVENTION

1. Field of the Invention

The present invention relates to a combined X-ray analysis apparatus combining the functions of X-ray fluorescence analysis and X-ray diffraction.

2. Description of the Related Art

Conventionally, elemental analysis and quantative analysis, and structural analysis, are carried out separately, with elemental analysis and quantative analysis being executed using an X-ray fluorescence analyzer and structural analysis being carried out using an X-ray diffractometer. In order to obtain accurate values when applying fundamental parameters (FP) in quantative methods employing logical operations in X-ray fluorescence analysis, it is necessary to set the structural elements of the sample in advance. In the case of quantative analysis where the sample is as yet unknown, the sample structure is estimated from the results of qualitative analysis using X-ray fluorescence and quantative analysis is then carried out. Alternatively, structural analysis is performed using analytical techniques such as X-ray diffraction, an accurate sample structure is then inputted from these results, and quantative analysis is performed using X-ray fluorescence analysis techniques.

A system is also adopted where an X-ray diffraction device mounted with a goniometer for an angular scanning method for detecting X-ray intensity at various angles by moving about prescribed angles and then stopping to achieve the above object is fitted with an EDX semiconductor detector is also adopted.

X-ray tubes applied to these devices typically have an anode target of Cu or Cr in the case of X-ray diffraction, and anode targets with comparatively high atomic numbers such as Mo or Rh in the case of X-ray fluorescence analyzers, although it is necessary for these targets to be selected depending on the purpose of the measurements.

Conventionally, X-ray fluorescence analyzers are utilized to perform elemental analysis but light elements cannot be discerned using the energy of fluorescent X-rays and with a typical energy distribution X-ray florescence analyzer, regarding the composition of each of the elements from Na which has an atomic number of 11 onwards, it could not be understood whether such compositions were oxides, nitrides or halogens. In the case of this kind of object, it is necessary to make a judgment by measuring a diffraction pattern using an X-ray diffractometer.

When an X-ray fluorescence analyzer apparatus and an X-ray diffraction apparatus are implemented in a single unit, the single X-ray detector adopts an angular scanning method for detecting X-ray intensity at various angles by moving to a prescribed angle and then stopping using a goniometer. This means that measurement requires time and installation space is required for the detection system. In order to combine the X-ray fluorescence detection system and the X-ray diffraction detection system, the path length for a primary X-ray irradiation system and a detection system for analyzing fluorescent X-rays has to be made long. This makes detection efficiency poor and means that a high-output X-ray generating source of more than a few kW has to be installed, which makes the apparatus large.

X-ray diffraction apparatus utilizing CCDs as linear or two-dimensional sensors, imaging plates or PSPC (Position-Sensitive Proportional Counters) are proposed in Japanese Patent Laid-open Application Nos. Hei. 6-258260, Hei. 9-72864, Hei. 10-48159, and Hei. 11-6806. However, these X-ray diffraction apparatus are targeted towards structural analysis such as pressure measurement, crystal orientation, degree of crystallinity, and do not give consideration to compatibility with elemental analysis.

When two types of analyzer, X-ray fluorescence analysis apparatus and X-ray diffraction apparatus, are installed individually, a larger footprint is required and measurement time is doubled. It is also necessary for the report for the apparatus to be divided into two types, which is problematic.

When an X-ray tube is used for both X-ray fluorescence analysis and X-ray diffraction, materials with a high atomic number such as Mo, Ag or Rh are most appropriate as the target material for the X-ray tube in the case of the X-ray fluorescence apparatus. The energy is then inappropriately high when these X-rays are utilized in X-ray diffraction and a Cu or Cr tube therefore has to be used in X-ray diffraction. This requires two types of tubes and causes the X-ray generating source to become big.

Implementing X-ray fluorescence analysis and X-ray diffraction using one apparatus is proposed in Japanese Patent Laid-open Application No. 2001-13095, but X-ray diffraction was inefficient when the X-ray source was an anode target targeted at X-ray fluorescence analysis.

SUMMARY OF THE INVENTION

A structural drawing of a system for resolving these problems is shown in FIG. 2. An energy distribution type X-ray detector 9 which is, for example, a PIN diode detector, and an analyzer 10 for detecting and performing qualitative/quantitative elemental analysis on fluorescent X-rays and a small CCD line sensor 6 and an analyzer 7 for performing structural analysis have a common X-ray high voltage source 15, X-ray tube 1, filter 2, collimator 3, sample stage 14, half-mirror 12, CCD camera for sample observation 13, and a control unit 11. There is no need to provide separation in the X-ray irradiation system from the X-ray tube 1 to the sample 4 because the X-ray detection system is small. This means that a fluorescent X-ray spectrum and an X-ray diffraction pattern can be obtained with the X-ray output at a low power of 100 W or less. A two layer structure of Cu on Mo is adopted as the anode target structure for the X-ray tube 1 in order to make both kinds of analysis more efficient. In the case of excitation using a low accelerating voltage, the operation of the X-ray tube 1 is such that generated Cu—K lines, Mo—L lines and continuous X-rays are shown monochromatically using a removably interposable Cu filter 2 located directly after the tube 1, with the obtained radiation quality (for Cu—K lines is put into the form of a fine beam using a collimator 3 for focusing x-rays to microscopic dimensions. This beam then irradiates a subject of measurement 4 placed on the sample stage 14, diffracted X-rays 5 generated as a result are angle-resolved and detected by the CCD line sensor 6, and X-ray structural analysis is executed. In the case of excitation using a high accelerating voltage, the aforementioned Cu filter is replaced with a removably interposable Mo or Zr filter, so that the Cu—K lines and Mo—L lines of the Mo—L lines, Mo—K lines and continuous X-rays thus generated are cut by absorption. The Mo—K lines and continuous X-rays thus obtained are then made into a fine beam by the collimator 3, and made to irradiate the subject to be measured 4 placed on the sample stage 14. The X-ray fluorescence 8 thus generated is then detected by the energy distribution type X-ray detector 9 and X-ray fluorescence analysis is executed.

An X-ray tube with a surface with an atomic number of 30 or less and a foundation with an atomic number of 40 or more is well known from Japanese Patent Publication No. Hei. 6-85308. However, the object of this well-known X-ray tube is to provide X-ray fluorescence analysis using efficient analysis for light elements to heavy elements but the object of the present invention is two different kinds of analysis of X-ray fluorescence analysis and X-ray diffraction, and differs in that a mechanism is provided for switching over the radiation quality for each type of X-ray characteristically generated by differences in excitation voltages depending on the purpose of the analysis.

A small, combined X-ray analysis apparatus having functions for inorganic X-ray fluorescence analysis and X-ray diffraction is therefore provided by adopting an X-ray source capable of selectively forming an X-ray beam and a small-type detection system.

BRIEF DESCRIPTION OF THE DRAWINGS

FIG. 2 shows a structural view of a combined X-ray apparatus having two functions of an X-ray diffraction function and an X-ray fluorescence function.

DETAILED DESCRIPTION OF THE INVENTION

Figure 1:
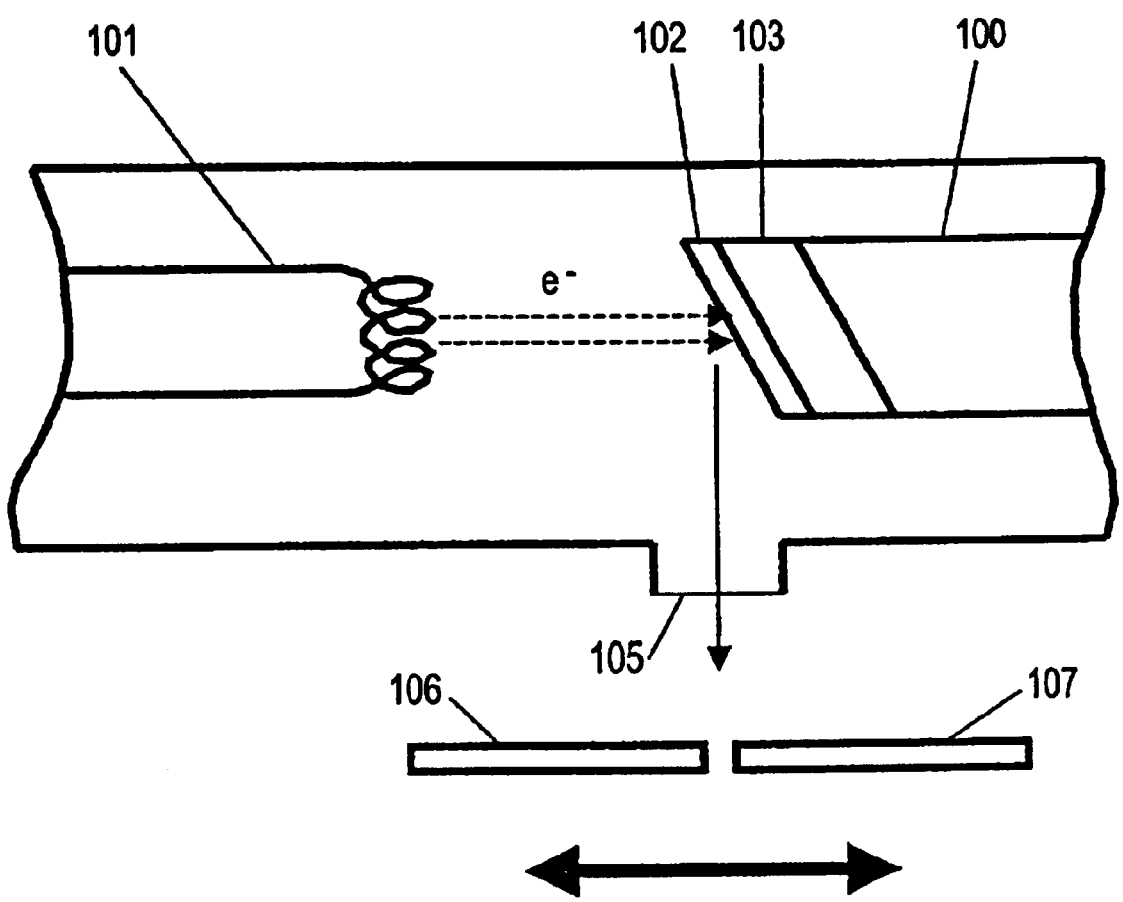
FIG. 1 shows an X-ray source for use in X-ray fluorescence analysis and X-ray diffraction measurement.

FIG. 1 shows an X-ray source capable of being utilized in both X-ray diffraction and X-ray fluorescence analysis. The anode target has a multi-layer structure comprising a first layer 103 constituted of Mo or Rh of a thickness of 0.05 to 0.5 mm on Cu 100 and a second layer 102 of Cu or Cr of a thickness of 0.005 to 0.015 mm placed thereon. A switchable accelerating voltage can be applied to the electron source 101 of the X-ray tube so that, for example, in the case of excitation using 15 kV as a low accelerating voltage, just Cu or Cr—K lines and continuous X-rays are generated from the port 105 without exciting 17 keV Mo—K lines. In this case, monochromicity is obtained by locating a Cu or Cr filter 106 or 107 directly after the tube so that X-ray diffraction conditions are then realized by fine focusing to an extent of 0.1 mm to 0.3 mm. FIG. 2 shows a structural drawing of this system.

Primary X-rays generated by the X-ray tube are made monochromatic by the filter 2 and the beam thus obtained is then finely focused by the collimator 3. This then passes through the half mirror 12 and irradiates the subject to be measured 4 placed on the sample stage 14. The generated diffracted X-rays 5 are then angle resolved and detected by the CCD line sensor 6 so that structural analysis employing X-ray diffraction is implemented. The position to be analyzed is then decided by observing an image depicted on the half-mirror 12 using a CCD camera.

When X-ray fluorescence analysis is carried out, utilization is possible in the measurement of elements other than Cu using Cu—K lines and elements other than Cr using Cr—K lines, and in particular, highly sensitive measurement of elements of atomic numbers of 28 or less is possible. Cu or Cr—K lines, Mo—K lines and continuous X-rays are generated under conditions of excitation using, for example, 50 kV as a high accelerating voltage when carrying out elemental analysis on elements of the atomic numbers of, for example, Ag or Sn. By then replacing the Cu or Cr filter 2 with a filter placed directly after the tube that allows Mo or Zr to pass, the low energy Cu or Cr—K lines are absorbed, and X-ray fluorescence analysis over a broad range of energy regions is possible by utilizing the Mo—K lines and the continuous X-rays. The subject of measurement 4 placed on the sample stage 14 is then irradiated with the beam obtained in this manner and X-ray fluorescence 8 generated by the subject to be measured 4 is detected by the energy distribution type detector 9. An accurate structure is then set up from the aforementioned results of the structural analysis and elemental analysis can be executed.

In this application, an X-ray generating system of a low output of 100 W or less shared, so that elemental analysis and structural analysis are possible using a single measuring head, enabling an X-ray diffraction function and an X-ray fluorescence function to be combined. This means that the installation space required for the device can be reduced or the device itself can be made small and portable. Further, accurate quantative analysis of inorganic matter can be implemented because both types of analysis are possible with one type of equipment, and the measurement time can therefore be made shorter.

What is claimed is:

1. A combined X-ray analysis apparatus for performing X-ray fluorescence analysis and X-ray diffraction analysis, comprising:

a shared portion used for performing X-ray fluorescence analysis and X-ray diffraction analysis and comprised of an X-ray high voltage power supply, an X-ray tube driven by the X-ray high voltage power supply to produce a primary X-ray beam, a shutter disposed in the path of the primary X-ray beam, a collimator for collimating the primary X-ray beam, a sample stage for supporting a sample in the path of the primary X-ray beam, a sample monitoring optical system for monitoring the sample, and a control unit for controlling the apparatus;

an energy distributed type X-ray detector disposed proximate the sample stage for detecting a fluorescent X-ray emitted by the sample in response to irradiation with the primary X-ray beam and subjecting the fluorescent X-ray to elemental qualative and quantative analysis of the sample; and a CCD sensor disposed proximate the sample stage for performing structural analysis of the sample;

wherein the control unit controls the X-ray high voltage power supply depending upon a type of analysis to be performed such that the high voltage power supply supplies a low acceleration voltage to the X-ray tube to emit a primary X-ray beam for performing X-ray diffraction using the CCD sensor, and supplies a high acceleration voltage to the X-ray tube to emit a primary X-ray beam for performing X-ray fluorescence analysis using the energy distributed type X-ray detector.

2. A combined X-ray analysis apparatus according to claim 1; wherein the X-ray tube has an anode target having a surface provided with a Cr or Cu thin film layer and a foundation layer thereunder formed of Mo or Rh; and further comprising a Cr or Cu filter-removably interposable between the X-ray tube and the collimator to produce monochromatic low energy Cr or Cu—K lines when a low acceleration voltage is supplied to the X-ray tube by the X-ray high voltage power supply so that an X-ray beam that can be used for X-ray diffraction is produced; and a Mo or Zr filter removably interposable between the X-ray tube and the collimator to absorb Cr or Cu—K lines when a high acceleration voltage is supplied to the X-ray tube by the X-ray high voltage power supply so that an X-ray beam that can be used for X-ray fluorescence analysis is produced.

3. A combined X-ray analysis apparatus according to claim 2; wherein the thickness of the Mo or Rh foundation layer is in the range of 0.05 mm to 0.5 mm, and the thickness of the Cu or Cr thin film layer is in the range of 0.005 mm to 0.015 mm.

4. An X-ray analysis apparatus for performing X-ray fluorescence analysis and X-ray diffraction analysis, comprising: an X-ray tube for generating a primary X-ray and having a multilayer target comprised of a thin film surface layer formed of Cr or Cu and a foundation layer under the surface layer formed of Mo or Rh a control unit for controlling the apparatus to supply a low acceleration voltage electron beam to the target to generate a primary X-ray for X-ray diffraction and a high acceleration voltage electron beam to the target to generate a primary X-ray for X-ray fluorescence analysis; a collimator for collimating the primary X-ray for irradiating a sample; an energy distribution type X-ray detector disposed proximate the sample for detecting a fluorescent X-ray emitted by the sample in response to irradiation with the primary X-ray and analyzing the fluorescent X-ray to perform elemental analysis of the sample; and a CCD sensor disposed proximate the sample for performing structural analysis of the sample.

5. An X-ray analysis apparatus according to claim 4; further comprising a pair of filters that are individually removably interposable between the X-ray tube and the collimator and comprising a first filter formed of Cr or Cu for producing monochromatic low energy Cr or Cu—K lines when a low acceleration voltage is applied to the target so that an X-ray beam that can be used for X-ray diffraction is output by the first filter, and a second filter formed of Mo or Zr for absorbing Cr or Cu—K lines so that an X-ray beam that can be used for X-ray fluorescence analysis is output by the second filter.

6. An X-ray analysis apparatus according to claim 4; wherein the thickness of the Mo or Rh foundation layer is in the range of 0.05 mm to 0.5 mm, and the thickness of the Cu or Cr thin film surface layer is in the range of 0.005 mm to 0.015 mm.

7. A combined X-ray analysis apparatus for performing X-ray fluorescence analysis and X-ray diffraction analysis, comprising:

a shared portion used for performing X-ray fluorescence analysis and X-ray diffraction analysis and comprised of an X-ray high voltage power supply, an X-ray tube driven by the X-ray high voltage power supply to produce a primary X-ray beam, a collimator for collimating the primary X-ray beam, a sample stage for supporting a sample in the path of the primary X-ray beam, and a control unit for controlling the apparatus;

an energy distributed type X-ray detector disposed proximate the sample stage for detecting a fluorescent X-ray emitted by the sample in response to irradiation with the primary X-ray beam and subjecting the fluorescent X-ray to elemental qualative and quantative analysis of the sample; and a CCD sensor disposed proximate the sample stage for performing structural analysis of the sample;

wherein the control unit controls the X-ray high voltage power supply depending upon a type of analysis to be performed such that the high voltage power supply supplies a low acceleration voltage to the X-ray tube to emit a primary X-ray beam for performing X-ray diffraction using the CCD sensor, and supplies a high acceleration voltage to the X-ray tube to emit a primary X-ray beam for performing X-ray fluorescence analysis using the energy distributed type X-ray detector.

8. A combined X-ray analysis apparatus according to claim 7; wherein the X-ray tube has an anode target having a surface provided with a Cr or Cu thin film layer and a foundation layer thereunder formed of Mo or Rh.

9. A combined X-ray analysis apparatus according, to claim 8; further comprising a Cr or Cu filter removably interposable between the X-ray tube and the collimator to produce monochromatic low energy Cr or Cu—K lines when a low acceleration voltage is supplied to the X-ray tube by the X-ray high voltage power supply so that an X-ray beam that can be used for X-ray diffraction is produced; and a Mo or Zr filter removably interposable between the X-ray tube and the collimator to absorb Cr or Cu—K lines when a high acceleration voltage is supplied to the X-ray tube by the X-ray high voltage power supply so that an X-ray beam that can be used for X-ray fluorescence analysis is produced.

10. A combined X-ray analysis apparatus according to claim 8; wherein the thickness of the Mo or Rh foundation layer is in the range of 0.05 mm to 0.5 mm, and the thickness of the Cu or Cr thin film layer is in the range of 0.005 mm to 0.015 mm.

* * * * *